(12) United States Patent
Meyer

(10) Patent No.: US 6,421,557 B1
(45) Date of Patent: Jul. 16, 2002

(54) METHOD FOR DETERMINING THE BAROREFLEX LATENT PERIOD AND BAROREFLEX SENSITIVITY

(75) Inventor: Wolfgang Meyer, Erlangen (DE)

(73) Assignee: Biotronik Mess-und Therapiegeräte GmbH & Co. Ingenieurbüro Berlin, Berlin (DE)

( * ) Notice: Subject to any disclaimer, the term of this patent is extended or adjusted under 35 U.S.C. 154(b) by 147 days.

(21) Appl. No.: 09/605,832

(22) Filed: Jun. 29, 2000

(30) Foreign Application Priority Data

Jun. 29, 1999 (DE) .......................... 199 29 705

(51) Int. Cl.$^7$ ..................... A61B 5/0452; A61B 5/0468
(52) U.S. Cl. ........................ 600/516; 600/515
(58) Field of Search ................... 600/515, 516, 600/518

(56) References Cited

U.S. PATENT DOCUMENTS 5,187,657 A  2/1993  Forbes ........................ 600/513
5,842,997 A  12/1998  Verrier et al. ................ 600/518

OTHER PUBLICATIONS

La Rovere et al, "Baroreflex Sensitivity and Heart–Rate Variability in Prediction of Total Cardiac Mortality After Myocardial Infarction," The Lancet, vol. 351, No. 9101, pp. 478–484.*

* cited by examiner

*Primary Examiner*—Carl Layno
(74) *Attorney, Agent, or Firm*—Browdy and Neimark

(57) ABSTRACT

A method for determining the baroreflex provides a non-invasive measurement of cardiac-interval periods, and a mathematical analysis of these measurement values on the basis of non-linear dynamic methods.

3 Claims, 6 Drawing Sheets

METHOD FOR DETERMINING THE BAROREFLEX LATENT PERIOD AND BAROREFLEX SENSITIVITY

BACKGROUND OF THE INVENTION

1. Field of the Invention

The invention relates to a method for deter the baroreflex latent period, and particularly the corresponding baroreflex sensitivity.

2. Background Art

The test of baroreflex sensitivity (BRS) has long been a common method with which the function of the circulatory system is tested within the scope of clinical tests (see two list of prior art, No. [4]). For example, the test is used to quality the risk of patients having acute myocardial infarction (see list of prior art, No. [5]).

The BRS is the ratio of the resulting drop in the heart rate to an increase in the arterial blood pressure due to medication. The method is thus invasive, and cannot be performed without some discomfort for the patient. In addition, the application, similarly to Valsalva's maneuver, or the decompression method (see list of prior art, No. [8]), which is controversial because of its low specificity, always requires outpatient treatment. A special evaluation procedure of the BRS test also permits conclusions about the latent period (see list of prior art, No. [6]), that is, the period between a drop in blood pressure and the response of the sino-atrial node due to the baroreflex but the procedure is far from conventional. A direct determination of the latent period from neural measurements as an exact method (see list of prior art, No. [7]) is highly invasive, and is therefore unsuitable for clinical diagnostics.

Recently, the baroreflex function has been indirectly incorporated through frequency analysis of the heart-rate variability, but this only encompasses the tonic partial aspect of the vagal activity (see list of prior art, No. [9]), or through the analysis of the heart-rate turbulence (see list of prior art, No. [10]). These two methods have a high prognostic value, but do not offer a direct measure for describing the baroreflex.

In contrast, in recent years, testing coupled systems in the field of non-linear dynamics has produced numerous methods and models for characterizing systems with an imminent time delay (see list of prior art, Nos. [11], [12]). Hence, it is also possible to reconstruct multi-dimensional systems by measuring a continuous variable (see list of prior art, No. [3]). Up to now, if the information about a system is present as interval data, however, only a partial reconstruction of the phase space has been possible, which can only be effected in strongly deterministic systems, with a sufficiently-long measuring period, in the stationary state (see list of prior art, No. [2]). Vital information about functional connections or an imminent time delay is not produced, however.

In addition, there are numerous models that simulate a heart-rate variability that is modulated by the baroreflex (see list of prior art, Nos. [13], [14]). One of these models is especially preferable, because it satisfies the requirement of factoring in the delay time of the baroreflex in a simple manner (see list of prior art, No. [1]). The model illustrates qualitatively-varying dynamic behavior, as a function of the time delay, with periodic, complex periodic and chaotic domains occurring.

Thus, two essential tools are available for testing new characterization methods of the baroreflex. On the one hand, it is possible to create a realistic, yet simple, model such that the dynamic processes triggered by changes in the latent period can be altered qualitatively to the greatest possible extent. On the other hand, methods of non-linear dynamics offer direct instruments for analyzing established model parameters exclusively from generated signals.

SUMMARY OF THE INVENTION

Starting from these set-ups, it is the object of the invention to permit a non-invasive, and therefore gentle, automatic testing and determination of the baroreflex latent period and, correspondingly, the baroreflex sensitivity, particularly using the carotid-sinus reflex.

According to the invention, in the method for determining the baroreflex latent period and, correspondingly, the baroreflex sensitivity, cardiac-interval periods, such as the P-P, P-R or R-R interval, are measured non-invasively, and the measured interval periods are mathematically analyzed according to non-linear dynamic methods.

The non-linear dynamic analysis method preferably comprises the following method steps:

the interpolation of the measured interval values for determining a continuous measured-value course from the discrete interval periods;

the graphing of the interpolated signal values in a three-dimensional phase space with the abscissas $y(t)$, $y(t-\tau)$ and $d(y)/d(t)$, with different baroreflex latent periods being assumed for the parameter $\tau$;

the projection of the three-dimensional graph into the two-dimensional space through the determination of all values on a sectional plane perpendicular to one of the axes, with $y(t)$ preferably being constant; and the determination of the assumed baroreflex latent period for which the highest order can be established in the two-dimensional projection as being relevant.

Checking whether the two-dimensional projection has an order is essentially the search for a line or course, as opposed to an "aggregate of points." For this purpose, the distances between points adjacent to a coordinate axis are added, with a minimal summation distance indicating a maximal order.

The proposed method is greatly simplified by the projection onto the two-dimensional space; the projection represents a type of scaling. A non-scalar, multi-dimensional set-up can also be advantageously employed, however, but such a set-up is associated with far more calculations.

The invention is described in detail below in conjunction with the attached drawings.

DESCRIPTION OF THE PREFERRED EMBODIMENT

The ensuing description first introduces the model and presents the reconstruction method in detail. Afterward, the reconstruction of the time delay of the model is discussed, and the model is simply switched to a triggered "beat-to-beat model," which is likewise reconstructed. The method is then applied to intracardial measurement data. Finally, the results are discussed, and the presented set-ups are further worked out particularly with respect to an automatic, non-invasive determination of the BRS, in addition to the latent period.

Figure 1:
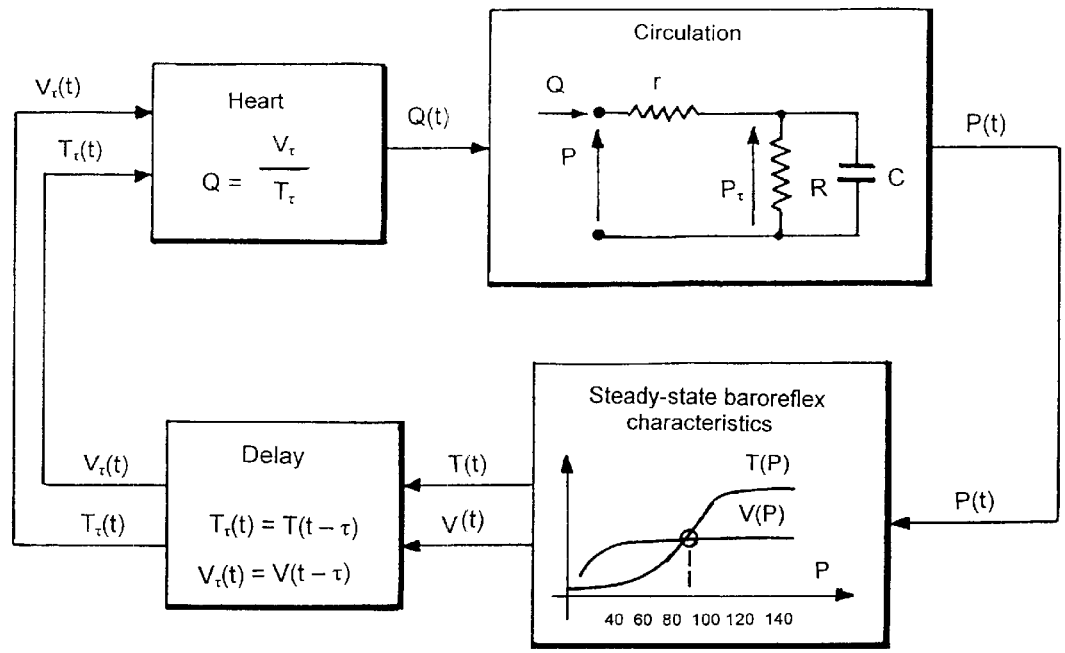
FIG. 1 is a graph of a so-called air-dome model, as is used as the basis for the method of the invention.

A simple air-dome set-up (FIG. 1) is the basis of the model. It leads to the following equations:

$$\frac{dP_g(t)}{dt} = \frac{1}{RC}[RQ(t) - P_g(t)]$$

$$P(t) = P_g(t) + rQ(t)$$

$$T(P) = T_g + \frac{T_m - T_g}{1 + \gamma e^{-\alpha P/P_g}}$$

$$V(P) = \frac{V_{max}}{1 + \beta\left(\frac{P}{P_v} - 1\right)^{-k}}$$

Figure 2:
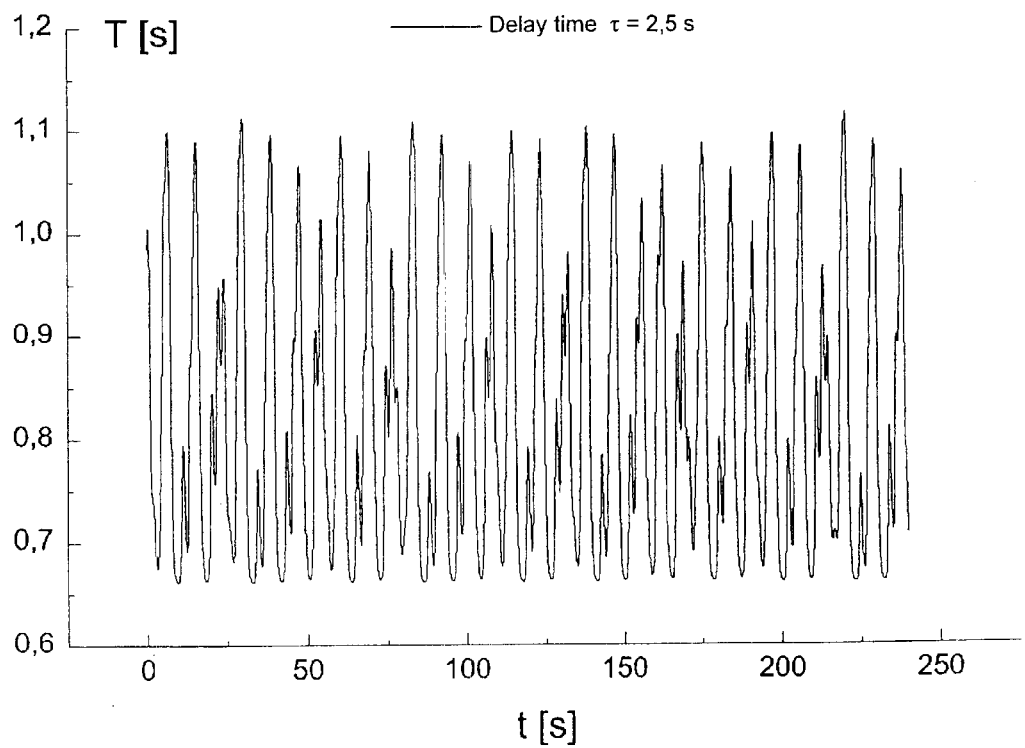
FIG. 2 is a curve graph for representing the course of the instantaneous cardiac period $T(t)$ with a delay time of $t=2.5$ s.

The model constants are determined from physiological measurement values according to [1]. The equations are integrated with step sizes of 0.01 according to the Euler method, with the time delay being varied in steps of 0.1 s between 1.5 s and 3.0 s the series tests in order to obtain time series with a different delay constant. The integration produces the signal of an instantaneous interval T(t) of an instantaneous stroke volume V(t) and an instantaneous pressure P(t). An example of a calculated course of T(t) with t=2.5 s following a response time is illustrated in FIG. 2 for comparison with [1].

According to [1], the model exhibits a chaotic deterministic behavior for the used parameter range, but this is not ascertained through a stringent analysis. The model also simulates complex-periodic oscillations and, by set-up, the frequency spectrum of a conventional time series of P-P or R-R intervals, despite a continuous cardiac period All of the used parameters up to the latent period are attributed to physiological measurements. The latent period in the chaotic partial space of the parameter set is typically set between 2 s and 3 s, within which a cascade of period duplications is assumed. From the existing literature, the setup of the latent periods does not appear tenable, but is secondary for the method presented here. The issue of how important a factor the form of the model used here represents is also of secondary importance. The sole decisive factor for the following reconstruction method is the tie delay, but not the explicit functional connection of the involved variables, as long as the coupling is given.

The reconstruction method is essentially effected according to the principles outlined in [3] and other publications of the same authors. The initial point for the considerations is the assumption of a time-delayed differential equation system of the form $$\dot{y}(t) = h(y(t), y(-\tau)),$$

with a degree of freedom y. The system, which is infinitely-dimensional because of the time delay, exists as a projection onto a three-dimensional phase space $$(y(t-\tau), y(t), \dot{y}(t)).$$

With y(t)=c, the three-dimensional system is projected onto a two-dimensional plane, i.e., a Poincaré section is performed. The delay time t is factored into the topology of a quantity of points $$(y(t-\tau), c, y(t))$$

that has been determined experimentally m this fashion. In the reconstruction, an assumption is made over this unknown delay time. A structure of the point quantity is formed in the plane, depending on the selected t; the further the selected delay time deviates from the actual delay time, or a multiple thereof the less regular the structure. The structure can be characterized, for example, by the fullness factor (the portion of phase-space cells occupied by points), or through simpler set-ups, such as the measurement of the length of the polygon connecting the points.

The principle can basically be applied to systems having more than one degree of freedom, such as the present baroreflex model. The above-described model can be brought into the aforementioned form, and is thus accessible for the described analysis. The precise implementation is primary a function of the form of the system and the number of degrees of freedom. Because only the latency is to be initially determined, however, a scalar set-up is performed in this test, which also appears to be practical, because in later applications only one state variable, namely the cardiac period, is also actually available.

Figure 3:
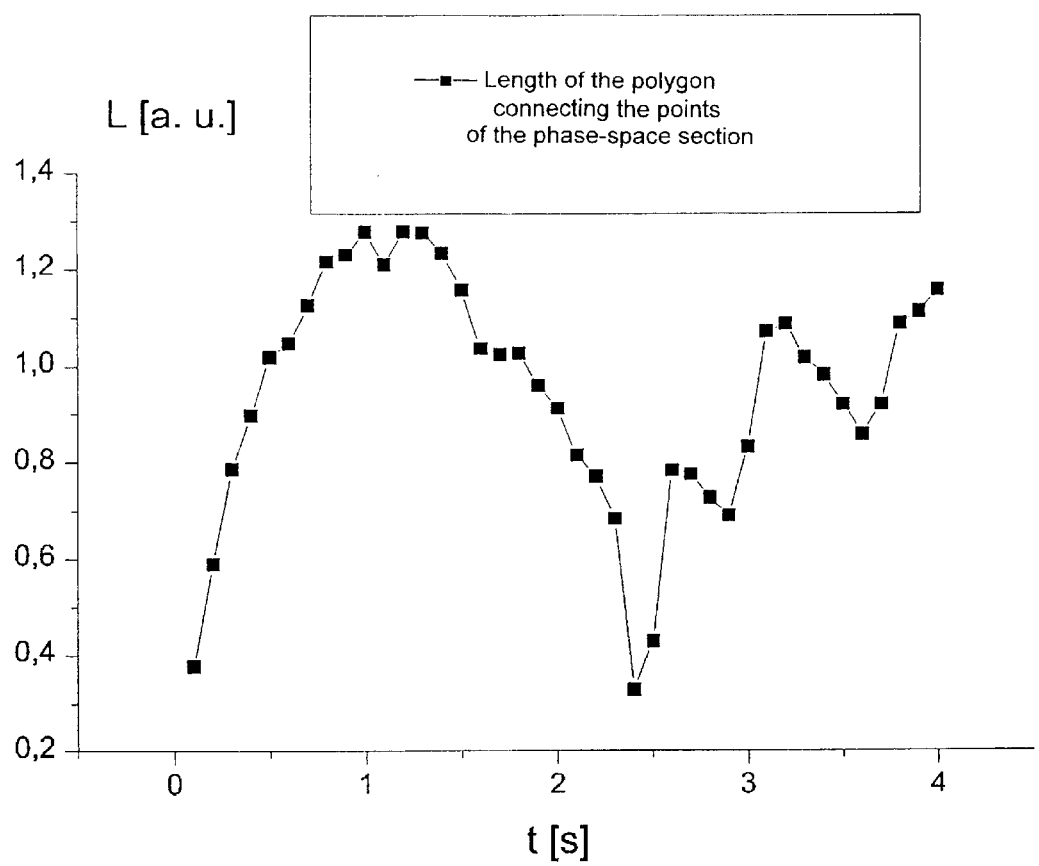
FIG. 3 is a curve graph for representing the polygon length L as a function of the assumed delay times t with an actual delay time of $\tau=2.5$ s.

The time delay is reconstructed as follows:

First, according to the above-described method, signal courses are generated with different delay times of 1.5 s to 3.0 s. With the use of the polygon method, all time series are analyzed in accordance with the described procedure. FIG. 3 illustrates a typical course of the resulting profile of the polygon length for a delay time of t=2.5 s as a function of the assumed delay time.

Based on the established profile, the delay time can be determined through the as sumption of the absolute minimum for the actual delay tie of t=2.4 s. The error of 0.1 s essentially results from the blurring of 0.1 s in the reconstruction. The error can be further reduced by a higher resolution in the reconstruction, or the consideration of the entire peak width, for example through a parabolic function adaptation.

Figure 4:
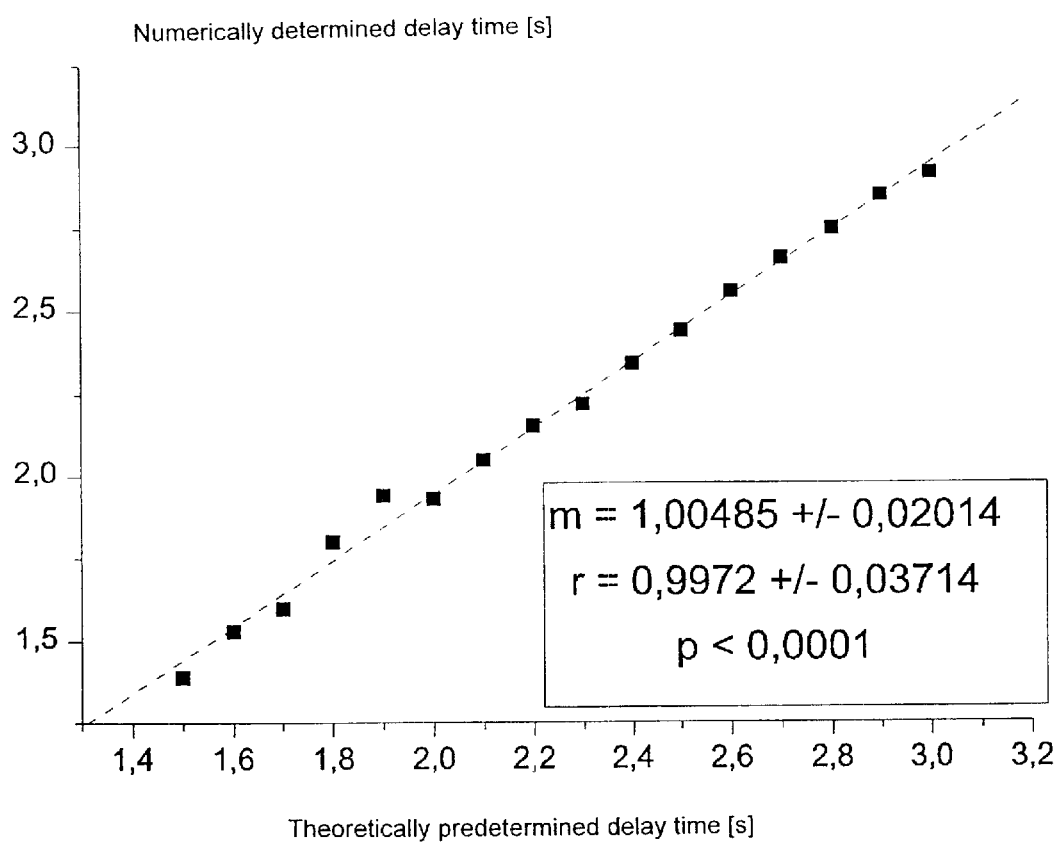
FIG. 4 is a curve graph for representing the match between the theoretically-predetermined delay time and the experimentally numerically-determined delay time.

FIG. 4 shows the correlation between the actual delay time and the delay the determined with the aid of the simple minimal method described above. An extensive matching between theoretical specification and the experimentally numerically-determined value can be seen The variation of the correlation coefficient from 1 is as slight as that of the slope of the regression lines. The correlation is highly significant.

The reconstruction in the beat-to-beat model is effected as follows:

The above-described reconstruction is effected with the use of the continuous signal course This course is, however, not available in the measurement of the cardiac period.

Figure 5:
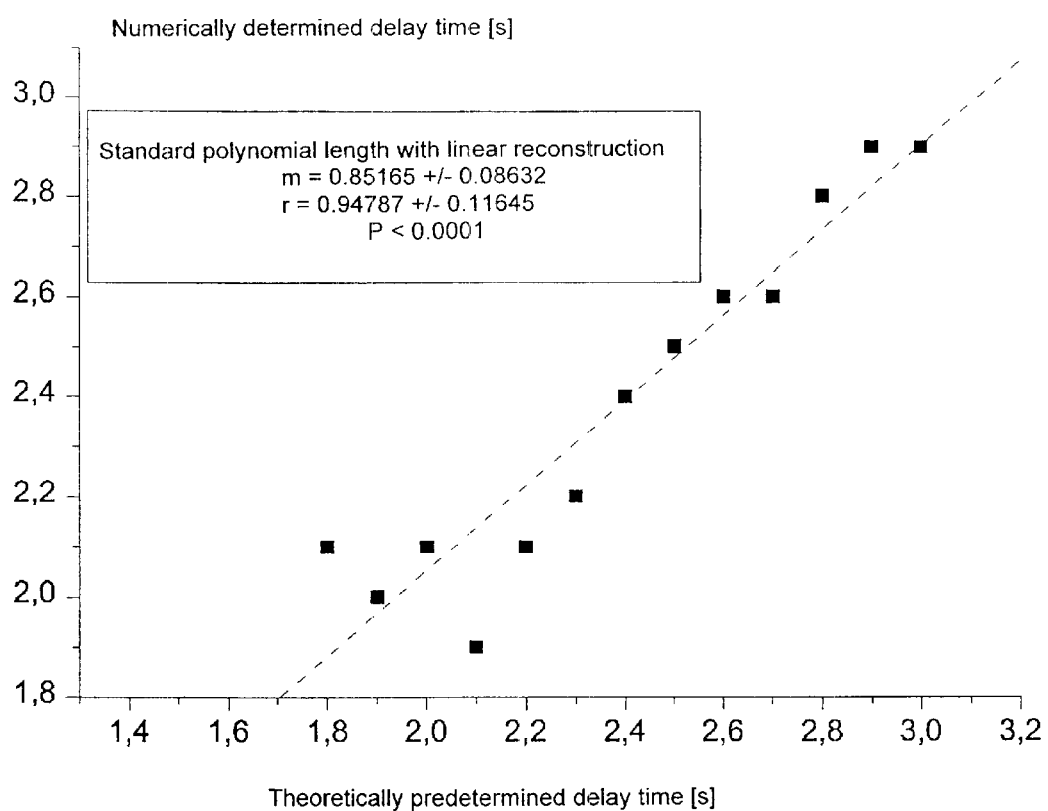
FIG. 5 is a curve diagram for representing the calculated time delay after the baroreflex model has been triggered by means of the integrate-and-fire method, and the determination of the instantaneous cardiac period by means of linear interpolation of the P-P intervals.

Instead, the determination of the intervals at the heart is an observation of a triggered activity. Therefore, the continuous model signal was first transformed into a time series of P-P intervals. For tis purpose, a simple integrate-and-fire model was used, with the reciprocal instantaneous cardiac period being interpreted as a dependent threshold value. For the reconstruction method to also be applicable to the generated intervals, the path of interpolation was followed, i.e., an instantaneous cardiac period was obtained through interpolation between the P-P intervals. With the time series generated in this fashion, which has a sampling rate of 100 Hz like the non-triggered original signal, the parameter of the polynomial length in the phase space was determined for different assumptions of the delay time, without further changes to the algorithmic process. The results for the different delay times are shown in FIG. 5.

Predetermined and experimentally numerically-determined time delays are also highly-significantly correlated in the linear interpolation of the P-P intervals after the previous triggering of the continuous baroreflex model by means of integrate-and-fire. The determination of the delay time was performed with an error of 0.3 s or 0.2 s only with values of t=1.8 s and t=2.1 s; no unambiguous identification of a delay time from the spectrum of polynomial lengths was recognizable for the preset times of 1.5 s to 1.7 s. Particularly in this case, further set-ups can improve the method, such as the implementation of a non-linear interpolation method.

A decisive factor for the applicability of the reconstruction method is not the ability of the parameters of the simulation to be reconstructed, but the ability of a latent period to be determined from cardiological measurement data that are additionally correlated with physiological conditions. The following discussion focuses on the results obtained with the simple method by way of intracardial measurement series.

The application of the theoretically-tested method represents an extensively empirical process. It is noted here that only occasional presumptions about the meaning of the latent period in contrast to the BRS are expressed in connection with pathological changes [6]. The comparison of the two following time series must therefore be considered in view of the limited knowledge about the feasibility of the reconstruction method, which is available for the first time through set-ups.

Figure 6:
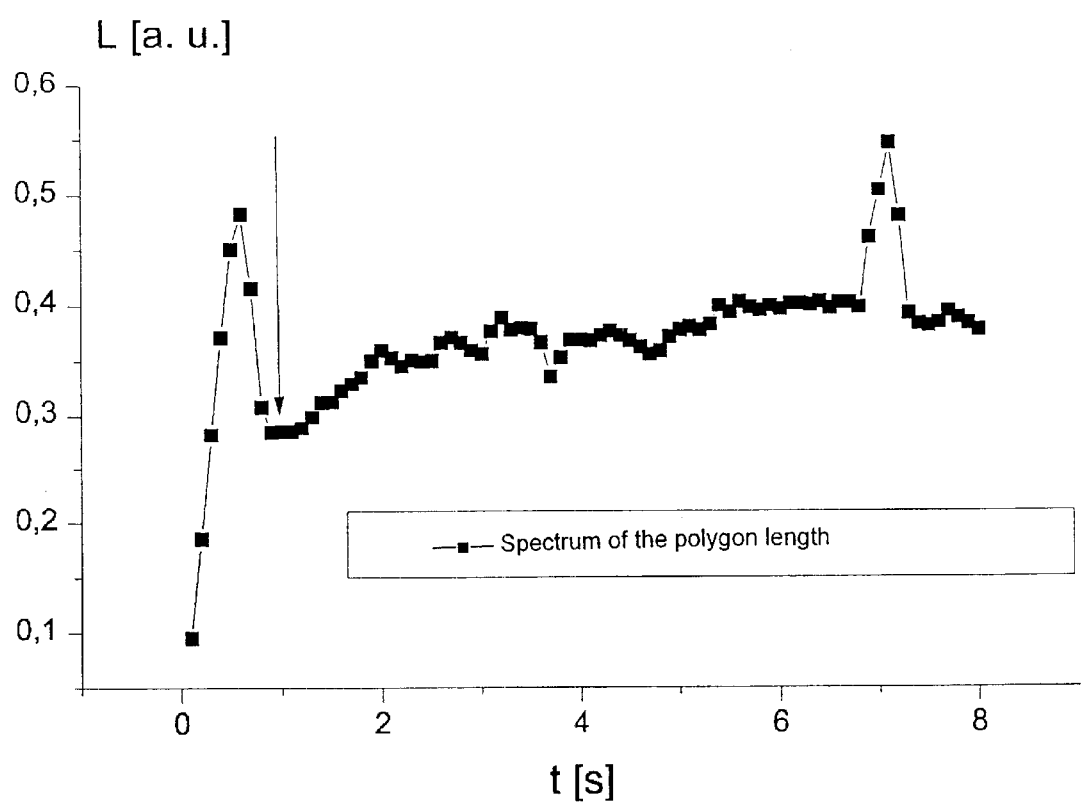
FIG. 6 is a curve diagram for representing the spectrum of the polygon length as a function of the assumed delay time for a time series of intracardial P-P intervals in a patient having no atrial extrasystoles.

The first time series was obtained through the measurement of intracardial ECG signals. The atrial ECG was triggered on the P wave; afterward, the obtained P-P intervals were interpolated and reconstructed. The measurement time was about 2 h; numerous non-stationary states of the circulatory system were assumed. FIG. 6 illustrates the spectrum of the polygon lengths for the entire time series.

After the spectrum of the polygon lengths has been interpreted, the time series is tolerable with a system of differential equations having a delay time of 1.0 s. The unambiguously identified minimum of tie spectrum is marked by an arrow.

The second time series was recorded over a time frame of similar length (about 2 h). The patient suffered from paroxysmal atrial fibrillation (PAF). The measurement was taken in a time segment in which no atrial extrasystoles occurred; following the evaluated segment, however, they occurred frequently. No fibrillations occurred at the time of the recording.

Figure 7:
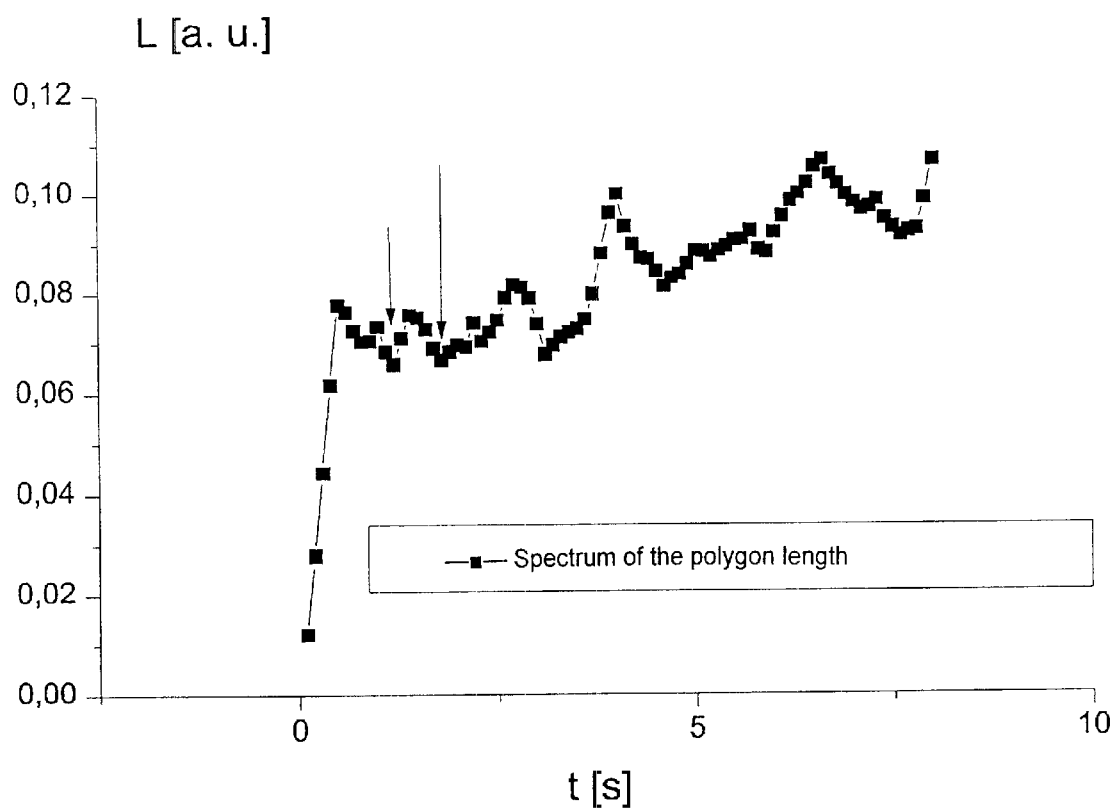
FIG. 7 is a curve diagram for representing the spectrum of the polygon length as a function of the assumed delay time for a time series of intracardial P-P intervals in a patient having PAF (not acute) during a period free from extrasystoles.

An unambiguous interpretation in terms of a delay time is difficult in the case of FIG. 7. While the first minimum and, at a short distance from it, the lowest minimum, are established at 1.2 s (short arrows the width of the associated trough is, nevertheless, hardly pronounced, unlike in FIG. 6. The second minimum (long arrow), in contrast, is wide at 1.8 s. In addition, of a higher order also occur at 3.4 s and 4.9 s, for example, so a delay time of t=1.7 can be assumed to be consistent. The result can therefore be interpreted as a tendency for the latent period to increase with a higher susceptibility for PAF or extrasystoles. The example reveals hat physiological time series are, as anticipated, more difficult to interpret than numerical simulations. Further set-up points for interpreting and improving the method can be derived from the differences between FIGS. 6 and 7.

Thus, the ambiguity of FIG. 7 indicates, on the one hand, an instability that can be attributed to pathologically-stipulated fluctuations in the latency. The weak exhibition of a primary minimum can be interpreted as a characteristic of a low baroreflex sensitivity, which is also expressed in a lack of a temporal correlation and a low heart-rate variability, as are detected with conventional methods in the same time series.

Basically, the two results can cautiously be interpreted as long as the method was not subjected to a comprehensive validation. This can only happen—in addition to the refinement of model presentations and the adaptation of existing systems—upon the discovery of a physiological correlative, i.e., a certain number of illnesses or comparison values that form a relationship with the latent period with stringent criteria for determining the latent period.

To summarize:

With the use of a cardiovascular model system of the baroreflex with a delay, and a method for reconstructing this delay time, it was seen that the methods known from non-linear dynamics can be applied to the model system This is also the case for the reconstruction of triggered time series. A systematic improvement in the method and its application to a wide range of cardiological time series are desirable.

The following literary citations are culled from the prior art:

[1] Cavalcanti, S., Belardinelli, E. Modeling of a Cardiovascular Variability Using a Differential Delay Equation, IEEE Trans. Biomed. Eng. 43: 992–989 (1996).

[2] Sauer, T., Reconstruction of Dynamical Systems from Interspike Intervals, Phys Rev. Lett 72; 3811–3814 (1994).

[3] Bünner, M. J., Meyer, Th., Kittel, A., Pansi J., Recovery of the time-evolution equation of time-delay systems from tie series, Phys. Rev. E 56: 5083–5089 (1997).

[4] LaRovere, M. T., Mortara, A., Schwartz, P. J., Baroreflex Sensitivity, J. Cardiovasc. Electrophysiol. 6: 761–774 (1995).

[5] LaRovere, M. T., Bigger, J. Th., Marcus, F. I., Morta A., Schwartz, P. J., Baroreflex sensitivity and heart-rate variability in prediction of total cardiac mortality after myocardial infarction, Lancet 351: 478–484 (1998).

[6] Smith, St. A., Stallard, T. J., Littler, W. A., Estimation of sinoaortic baroreceptor heart rate sensitivity and latency in a new microcomputer assisted method of analysis, Cardiovasc. Res. 20: 877–882 (1986).

[7] Fagius, J., Sundlöf, G., Wallin B. G., Variation of sympatetic reflex latency in man, J. Auton. Nev. Syst. 21: 157–165 (1987).

[8] Potts, I., Raven, P. B., Effect of dynamic exercise on human carotid-cardiac baroreflex latency, Am. J. Physiol. 268; H1208–H1214 (1995).

[9] DeFerrari G. M., Landolina, M., Mantica, M., Manfredini, R., Schwartz, P. J., Lotto, A. Baroreflex sensitivity, but not heart rate variability, is reduced in patients with life-threatening ventricular arrhythmias long after myocardial infarction, Am. Heart J. 130: 473–480 (1995).

[10] Schmidt, G., Malik, M., Barthel, P., Schneider, R., Ulm, K, Rolnitzky, L., Camm, A. J., Bigger, J. Th., Schömig, A., Heart-rate turbulence after ventricular premature beats as a predictor of mortality after acute myocardial infarction, Lancet 353: 1390–1396 (1999).

[11] Bünner, M. J., Popp, M., Meyer, Th, Kittel, A., Rau, U., Parisi J., Recovery of scalar time-delay from time series, Phys. Lett. A 211: 345–349 (1996).

[12] Bünner, M. J., Popp, M., Meyer, Th., Kittel, A, Parisi J., Tool to recover scalar time-delay systems from experimental time series, Phys. Rev. E 54: R3082–R3085 (1996).

[13] DeBoer, R. W., Karemaker, J. M., Strackee, J., Hemodynamic fluctuations and baroreflex sensitivity in humans: a beat-to-beat model, Am. J. Physiol. 253: 680–689 (1987).

[14] Seidel H., Herzel, H., Modelling Heart Rate Variability due to Respiration and Baroreflex, pre print.

What is claimed is

1. A method for determining A baroreflex latent period, particularly A corresponding baroreflex sensitivity, comprising a non-invasive measurement of cardiac-interval periods, and a mathematical analysis of measurement values of the cardiac-interval periods on the basis of non-linear dynamic methods.

2. The method according to claim 1, wherein the non-linear dynamic analysis method comprises following steps:

an interpolation of the interval measurement values for determining a continuous measurement-value course from the discrete interval periods;

a graphing of the interpolated signal values in a three-dimensional phase space with abscissas $y(t)$, $y(t-\tau)$ and $d(y)/d(t)$ with different baroreflex latent periods being assumed for a parameter $\tau$;

a projection of the three-dimensional graph into a two-dimensional space through a determination of all values on a sectional plane perpendicular to one of the axes, with $y(t)$ preferably being constant; and a determination of an assumed baroreflex latent period for which a highest order can be established in the two-dimensional projection as being relevant.

3. The method according to claim 1, wherein the P-P, P-R and/or R-R cardiac intervals are measured non-invasively.

* * * * *